US011319561B2

(12) United States Patent
Xu et al.

(10) Patent No.: US 11,319,561 B2
(45) Date of Patent: May 3, 2022

(54) METHOD FOR PRODUCING A LONG CHAIN DICARBOXYLIC ACID BY FERMENTATION, FERMENTATION BROTH, TREATED FERMENTATION BROTH AND WASTEWATER

(71) Applicants: Cathay Biotech Inc., Shanghai (CN); CIBT America Inc., Newark, DE (US)

(72) Inventors: Min Xu, Shanghai (CN); Chen Yang, Shanghai (CN); Bingbing Qin, Shanghai (CN); Naiqiang Li, Shanghai (CN); Xiucai Liu, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 76 days.

(21) Appl. No.: 16/207,721

(22) Filed: Dec. 3, 2018

(65) Prior Publication Data

US 2019/0271012 A1  Sep. 5, 2019

(30) Foreign Application Priority Data

Mar. 1, 2018  (CN) .......................... 201810169684.6

(51) Int. Cl.
| | | |
|---|---|---|
| C12P 7/64 | (2022.01) | |
| C07C 55/02 | (2006.01) | |
| C12P 7/6409 | (2022.01) | |
| C12P 7/44 | (2006.01) | |

(52) U.S. Cl.
CPC ............ *C12P 7/6409* (2013.01); *C07C 55/02* (2013.01); *C12P 7/44* (2013.01)

(58) Field of Classification Search
None
See application file for complete search history.

(56) References Cited

U.S. PATENT DOCUMENTS

| | | | | |
|---|---|---|---|---|
| 4,339,536 A * | 7/1982 | Kato | ........................ | C12N 1/28 435/142 |
| 9,012,187 B2 * | 4/2015 | Jansen | ...................... | C12P 7/44 435/145 |
| 9,388,378 B2 * | 7/2016 | Liu | ........................... | C12R 1/72 |
| 2013/0116471 A1* | 5/2013 | Yan | .......................... | C07C 51/42 562/593 |
| 2014/0228586 A1* | 8/2014 | Beardslee | ............ | C12N 15/815 554/121 |

FOREIGN PATENT DOCUMENTS

| | | | |
|---|---|---|---|
| CN | 1071951 A | * | 5/1993 |
| CN | 107326051 A | | 11/2017 |
| EP | 3438271 A2 | | 2/2019 |
| WO | 2018010057 A1 | | 1/2018 |

OTHER PUBLICATIONS

Liu, Shuchen; et al; "Optimal pH control strategy for high-level production of long-chain[alpha],[omega]-dicarboxylic acid by Candida tropicalis" Enzyme and Microbial Technology, 34, 73-77, 2004 (Year: 2004).*
Uchio, Ryosuke; Shiio, Isamu; "Microbial Production of Long-chanin Dicarboxylic Acids from n-Alkanes: Part II. Production by Candida cloacae Mutant Unable to Assimilate Dicarboxylic Acid" Agricultural and Biological Chemistry,36, 426-433, 1972 (Year: 1972).*
Clomburg et al., Integrated engineering of β-oxidation reversal and ω-oxidation pathways for the synthesis of medium chain ω-functionalized carboxylic acids. Metabolic Engineering, 2015, vol. 28, pp. 202-212.
Wang et al., Development of mazF-based markerless genome editing system and metabolic pathway engineering in Candida tropicalis for producing long-chain dicarboxylic acids. Journal of Industrial Microbiology & Biotechnology, 2018, vol. 45, pp. 971-981.
Han et al., Designing and Creating a Synthetic Omega Oxidation Pathway in *Saccharomyces cerevisiae* Enables Production of Medium-Chain α, ω-Dicarboxylic Acids. Fontiers in Microbiology, Nov. 7, 2017, vol. B, pp. 1-12.
Werner et al., Neue Biokatalysatoren zur Herstellung langkettiger Dicarbonsäuren. BioSpektrum, Jun. 2017, pp. 706-708.
Liu et al., Intracellular pH and Metabolic Activity of Long-Chain Dicarboxylic Acid-Producing Yeast *Candida tropicalis*. Journal of Bioscience and Bioengineering, 2003, vol. 96, No. 4, pp. 349-353.
Abghari et al., Combinatorial Engineering of Yarrowia lipolytica as a Promising Cell Biorefinery Platform for the de novo Production of Multi-Purpose Long Chain Dicarboxylic Acids. Fermentation, 2017, vol. 3, No. 40, pp. 1-30.
Extended European Search Report issued for European Patent Application No. 18212782.9 dated Jun. 7, 2019, 14 pages.

* cited by examiner

*Primary Examiner* — David W Berke-Schlessel
(74) *Attorney, Agent, or Firm* — Rothwell, Figg, Ernst & Manbeck, P.C.

(57) ABSTRACT

The present invention discloses a method for producing a long chain dicarboxylic acid by fermentation as well as a fermentation broth, a treated fermentation broth and a wastewater. The salt content in the fermentation broth is controlled to be below 20% by the fermentation method of the present invention. The method for producing a long chain dicarboxylic acid by fermentation provided by the present invention can effectively reduce the amount of alkali used in the fermentation process and the amount of acid used in the subsequent extraction of the long chain dicarboxylic acid, thereby reducing the amount of salt in the whole production process of the long chain dicarboxylic acid. At the same time, the method of the present invention also has many advantages such as shortening the fermentation time, increasing the acid production, reducing the amount of medium, and suitable for the production of various types of long-chain dicarboxylic acids, etc. Compared with the existing production process, the method of the present invention not only has significant cost advantages, but also can effectively reduce the pressure on resource and environment, thus it has a very obvious value advantage in industrialization.

20 Claims, No Drawings

METHOD FOR PRODUCING A LONG CHAIN DICARBOXYLIC ACID BY FERMENTATION, FERMENTATION BROTH, TREATED FERMENTATION BROTH AND WASTEWATER

CROSS-REFERENCE TO RELATED APPLICATIONS

This application claims priority to Chinese Patent Application No. 201810169684.6 filed on Mar. 1, 2018, the entire contents of which are incorporated herein by reference.

FIELD OF THE INVENTION

The present invention relates to a method for producing a long chain dicarboxylic acid (LCDA) by fermentation as well as a fermentation broth, a treated fermentation broth and a wastewater.

BACKGROUND OF THE INVENTION

Long chain dicarboxylic acid (LCDA) has a general formula (HOOC(CH$_2$)nCOOH, n≥7) and has a very wide range of applications. Long chain dicarboxylic acid as raw material can be used to synthesize special nylons, high-grade perfumes, high-grade hot melt adhesives, cold resistant plasticizers, high-grade lubricating oils, high-grade rust inhibitors, high-grade paints and coatings, etc. Long chain dicarboxylic acid can usually be synthesized chemically or biologically. The chemical synthesis route is long. The reaction requires high temperature and high pressure, and the requirement for catalyst is critical. Therefore, there are fewer varieties of long chain dicarboxylic acids on an industrial scale, and only a few varieties of 12-carbon long chain dicarboxylic acids. The biological method uses a long chain alkane as substrate to obtain a long chain dicarboxylic acid by microbiological conversion. The production process is under normal temperature and pressure. A variety of long chain dicarboxylic acids (e.g. from C9 to C18) can be produced in large scale.

Biological methods for producing a long chain dicarboxylic acid have been studied for many years. A strain that can produce a long chain dicarboxylic acid was firstly screened from the oil field by researchers, and the strain was mutagenized to increase the yield of long chain dicarboxylic acid. The key enzymes in the synthesis process of a long chain dicarboxylic acid are also studied by some researchers. Most of the literatures about the study on long chain dicarboxylic acid abroad are to genetically modify bacterial strains to increase the yield of product by blocking or weakening related enzymes involved in fatty acid β-oxidation and enhancing the enzymes involved in fatty acid α-ω-oxidation. Published patents such as CN 1071951A, CN 1067725C, CN 1259424C, 200410018255.7, 200610029784.6 provide methods for producing a long chain dicarboxylic acid by microbial fermentation. All these methods have the following problems: a large amount of alkali is required to be added during the fermentation, and then a large amount of acid is required in order to obtain a product of a long chain dicarboxylic acid. In one hand, the inputs of alkali and acid increase the production cost, and on the other hand, a salt is produced in the reaction of acid and alkali, and the presence of salt increases costs of manpower and material resources in the post-treatment process, and the desalting process is very complicated and improper treatment has a very negative impact on environment.

Therefore, under the premise of ensuring the acid production and the rate of acid production, how to reduce the salt content in the fermentation broth as much as possible, which facilitates the subsequent treatment process and does not increase the environmental pressure, is a very practical problem that needs to be solved in the prior art.

SUMMARY OF THE INVENTION

A large amount of an inorganic salt will be produced in the process of producing a long chain dicarboxylic acid, which is mainly because much alkali is required to be added during the fermentation, and a large amount of acid is required to be added during the crystallization of a long chain dicarboxylic acid, and then a salt is formed due to the reaction of acid and alkali.

For a fermentation process, in order to make a long chain dicarboxylic acid to exist in the form of a water-soluble salt of the dicarboxylic acid, and to maintain a good mass transfer in the fermentation process, all existing conventional methods for producing a long chain dicarboxylic acid by fermentation require the fermentation performed under an alkaline condition. At the same time, in the fermentation process, with the increased accumulation of a long chain dicarboxylic acid, a large amount of alkali is needed to be added to neutralize the produced long chain dicarboxylic acid to ensure the balance of the fermentation system.

A large amount of acid is needed to be added in the crystallization process of a long chain dicarboxylic acid. As a long chain dicarboxylic acid exists in the form of a salt in the fermentation broth after completion of the fermentation, a large amount of acid is needed to be added in the process of extraction and purification of the dicarboxylic acid to convert the salt of the long chain dicarboxylic acid in the system into a product of the long chain dicarboxylic acid.

The above inputs of alkali and acid cause the concentration of the salt in the treated fermentation broth system to be as high as 50000-70000 μg/ml (50000-70000 ppm). This high-salt wastewater is difficult to handle, which is a very important challenge to the environment and seriously affects the development of the industry of producing a long chain dicarboxylic acid by biological methods.

In order to overcome the defects in the existing production process of a long chain dicarboxylic acid, the present invention provides a method for producing a long chain dicarboxylic acid by fermentation, a fermentation broth and a treated fermentation broth thereof, and a wastewater produced by the method for producing a long chain dicarboxylic acid.

One object of the present invention is a method for producing a long chain dicarboxylic acid by fermentation, wherein the content of salt in the fermentation broth of the fermentation is below 20%, preferably below 15%, and more preferably below 10%, wherein the percentage is a mass percentage relative to the total amount of the long chain dicarboxylic acid produced by fermentation.

In a preferred embodiment of the present invention, the salt comprises, but not limited to, one or more of potassium salt, sodium salt, magnesium salt, calcium salt, iron salt, ammonium salt, hydrochloride, carbonate, sulfate, nitrate and phosphate.

In a preferred embodiment of the present invention, the content of salt in the fermentation broth may be 20%, 19%, 18%, 17%, 16%, 15%, 14%, 13%, 12%, 11%, 10%, 9%, 8%, 7%, 6%, 5%, 4%, 3%, 2%, and 1%, wherein the percentage is a mass percentage relative to the total amount of the long chain dicarboxylic acid produced by fermentation.

In the present invention, the salt in the fermentation broth may be a salt contained in the fermentation medium, or a salt produced due to pH adjustment.

In the production method according to the present invention, the fermentation process comprises trophophase and conversion phase (acid-producing phase).

In a preferred embodiment of the present invention, the pH during the trophophase of the fermentation is above 3.0, and preferably between 3.5 and 6.5.

In a preferred embodiment of the present invention, the pH during the conversion phase of the fermentation is below 7.0, preferably between 4.0 and 6.8, and more preferably between 5.0 and 6.5.

In a preferred embodiment of the present invention, the pH of the fermentation system is controlled to be below 7.0, preferably between 4.0 and 6.8, and more preferably between 5.0 and 6.5, when the cell optical density ($OD_{620}$) is above 0.5 (diluted 30 times) during the fermentation.

In the present invention, the fermentation is performed under an acidic condition, so that the amount of alkali to be added in the fermentation process is greatly reduced, and the salt content in the fermentation broth, the treated fermentation broth and the wastewater is greatly reduced. At the same time, the present invention can also ensure good fermentation conversion rate and higher acid production under the above pH conditions.

In a preferred embodiment of the present invention, the temperature of the fermentation is between 28 and 32° C.

In a preferred embodiment of the present invention, the aeration rate of the fermentation is between 0.3 and 0.7 vvm.

In a preferred embodiment of the present invention, the pressure of the fermentation is between 0.05 and 0.14 MPa.

In a preferred embodiment of the present invention, the dissolved oxygen (DO) in the conversion process of the fermentation is not less than 15%.

In a preferred embodiment of the present invention, 0% to 3% alkane is added at the start of the fermentation.

In a preferred embodiment of the present invention, the inoculum amount of the fermentation is between 10% and 30%.

In a preferred embodiment of the present invention, a substrate is added for fermentation conversion when the strain is cultured to a cell optical density ($OD_{620}$) of above 0.5 (diluted 30 times).

In a preferred embodiment of the present invention, the strain for fermentation comprises *Candida tropicalis* or *Candida sake*, preferably *Candida tropicalis* (Deposit No. CCTCC M203052), or *Candida tropicalis* CATN145 (Deposit No. CCTCC M 2011192), or *Candida sake* CATH4013 (Deposit No. CCTCC M2011486), or *Candida tropicalis* CAT H1614 (Deposit No. CCTCC M 2013143), or *Candida sake* CATH4014 (Deposit No. CCTCC M2011487), or *Candida sake* CATH4012 (Deposit No. CCTCC M2011485), or *Candida sake* CATH4016 (Deposit No. CCTCC M2011488), or *Candida sake* CATH430 (Deposit No. CCTCC M2011489).

In a preferred embodiment of the present invention, the fermentation medium comprises a carbon source, a nitrogen source, an inorganic salt, and a nutritional factor.

Among them, the carbon source comprises one or more of glucose, sucrose and maltose; and the amount of the carbon source added is preferably from 1% to 10% (w/v).

Among them, the nitrogen source comprises one or more of peptone, yeast extract, corn steep liquor, ammonium sulfate, urea and potassium nitrate; and the total amount of the nitrogen source added is preferably from 0.1% to 3% (w/v).

Among them, the inorganic salt comprises one or more of potassium dihydrogen phosphate, potassium chloride, magnesium sulfate, calcium chloride, ferric chloride and copper sulfate; and the total amount of the inorganic salt added is preferably from 0.1% to 1.5% (w/v).

Among them, the nutritional factor comprises one or more of vitamin B1, vitamin B2, vitamin C and biotin; and the total amount of the nutritional factor added is preferably from 0% to 1% (w/v).

In a preferred embodiment of the present invention, the fermentation medium comprises the following ingredients: glucose 1% to 5%, corn steep liquor 0.1% to 0.9%, yeast extract 0.1% to 0.5%, potassium nitrate 0.05% to 1.2%, potassium dihydrogen phosphate 0.05% to 1.0%, urea 0.05% to 0.3%, ammonium sulfate 0.05% to 0.3%, and sodium chloride 0.05% to 0.2% (w/v).

In a preferred embodiment of the present invention, the fermentation medium further comprises the following ingredients: glucose 1% to 5%, potassium nitrate 0.05% to 0.6%, potassium dihydrogen phosphate 0.02% to 0.6%, ammonium sulfate 0.05% to 0.3%, and magnesium sulfate 0.05% to 0.3% (w/v).

In a preferred embodiment of the present invention, a secondary carbon source can be fed in the fermentation process, and the secondary carbon source can be fed in batch or continuous mode. The secondary carbon source comprises sucrose or glucose. The concentration of the secondary carbon source is from 10% to 70%. The sugar concentration in the fermentation conversion system is controlled to be from 0.1% to 1% (w/v) by feeding a secondary carbon source.

According to common knowledge in the field of fermentation, the percentage in the present invention is mass/volume ratio, i.e. w/v; % represents g/100 mL.

In a preferred embodiment of the present invention, the substrate for the fermentation comprises an alkane, preferably C9 to C22 normal alkane, more preferably C9 to C18 normal alkane, and most preferably C10, C11, C12, C13, C14, C15 or C16 normal alkane.

In a preferred embodiment of the present invention, the long chain dicarboxylic acid comprises C9 to C22 long chain dicarboxylic acid, preferably comprises C9 to C18 long chain dicarboxylic acid, and more preferably comprises one or more of sebacic acid, undecanedioic acid, dodecanedioic acid, brassylic acid, tetradecanedioic acid, pentadecanedioic acid, and hexadecanedioic acid.

Another object of the present invention is a fermentation broth of a long chain dicarboxylic acid, wherein the content of salt in the fermentation broth is below 20%, preferably below 15%, and more preferably below 10%, wherein the percentage is a mass percentage relative to the total amount of the long chain dicarboxylic acid produced by fermentation.

In a preferred embodiment of the present invention, the salt comprises, but not limited to, one or more of potassium salt, sodium salt, magnesium salt, calcium salt, iron salt, ammonium salt, hydrochloride, carbonate, sulfate, nitrate and phosphate.

In a preferred embodiment of the present invention, the salt content in the fermentation broth may be 20%, 19%, 18%, 17%, 16%, 15%, 14%, 13%, 12%, 11%, 10%, 9%, 8%, 7%, 6%, 5%, 4%, 3%, 2%, and 1%, wherein the percentage is a mass percentage relative to the total amount of the long chain dicarboxylic acid produced by fermentation.

According to common knowledge in the art, the total long chain dicarboxylic acid produced by fermentation comprises a crystal of a long chain dicarboxylic acid; or may also comprise a long chain dicarboxylic acid precipitated in amorphous form; or may also comprise very few long chain dicarboxylic acids precipitated in the form of a salt, or may also comprise very few long chain dicarboxylic acids in dissolved state in the form of a salt present in the solution.

In a preferred embodiment of the present invention, the fermentation broth of a long chain dicarboxylic acid is a fermentation broth of a long chain dicarboxylic acid obtained by fermentation conversion under an acidic condition.

In a preferred embodiment of the present invention, the fermentation broth of a long chain dicarboxylic acid is a fermentation broth of a long chain dicarboxylic acid obtained by fermentation conversion at a pH below 7.0, preferably from 4.0 to 6.8, and more preferably from 5.0 to 6.5.

In a preferred embodiment of the present invention, the salt in the fermentation broth comprises an inorganic salt and a salt of dicarboxylic acid. Among them, the inorganic salt accounts for the majority, and the salt of dicarboxylic acid accounts for very little. The salt of dicarboxylic acid generally exists in the form of a sodium salt of the dicarboxylic acid.

Still another object of the present invention is a treated fermentation broth of a long chain dicarboxylic acid, wherein the salt content in the treated fermentation broth is below 12000 ppm, and the parts per million is the parts per million by mass of the salt to the treated fermentation broth of a long chain dicarboxylic acid.

In a preferred embodiment of the present invention, the treated fermentation broth is a mixed solution obtained after removing the solid in the fermentation broth. The solid comprises particles of the long chain dicarboxylic acid; alternatively, the solid comprises particles of the long chain dicarboxylic acid and cells. The treated fermentation broth may or not comprise a cell. The particle of the long chain dicarboxylic acid comprises a large amount of crystals of long chain dicarboxylic acids as well as long chain dicarboxylic acids in amorphous form, or may also comprise very few solids of long chain dicarboxylic acids present in the form of salts, etc.

Among them, the pH of the acidification is preferably from 2.5 to 5, and more preferably from 3 to 4, and may be 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0. The acidification is preferably performed by using sulfuric acid. The method for removing the solid comprises centrifugation or filtration.

In a preferred embodiment of the present invention, the salt in the treated fermentation broth of a long chain dicarboxylic acid comprises, but not limited to, one or more of potassium salt, sodium salt, magnesium salt, calcium salt, iron salt, ammonium salt, hydrochloride, carbonate, sulfate, nitrate and phosphate. The salt in the treated fermentation broth of a long chain dicarboxylic acid comprises an inorganic salt, and may also comprise very few soluble salt of a long chain dicarboxylic acid.

Specifically, the salt content in the treated fermentation broth may be 12000 ppm, 11000 ppm, 10000 ppm, 9000 ppm, 8000 ppm, 7000 ppm, 6000 ppm, 5000 ppm, 4000 ppm, 3000 ppm, 2000 ppm, or 1000 ppm.

In a preferred embodiment of the present invention, the salt content in the treated fermentation broth is below 7000 ppm.

In a preferred embodiment of the present invention, the salt in the treated fermentation broth comprises an inorganic salt. The inorganic salt accounts for the majority of the total salts. The salt in the treated fermentation broth may also comprise a salt of a dicarboxylic acid. The salt of a dicarboxylic acid accounts for very little of the total salts.

Yet another object of the present invention is a wastewater produced by a method for producing a long chain dicarboxylic acid by fermentation, wherein the salt content in the wastewater is below 12000 ppm, and the parts per million is the parts per million by mass of the salt to the wastewater.

The wastewater is a liquid that enters a wastewater treatment system, obtained by removing the cell and long chain dicarboxylic acid in the above fermentation broth of a long chain dicarboxylic acid.

According to common knowledge in the art, the wastewater is generally obtained by the following methods: acidifying the fermentation broth and removing the solid to obtain a treated fermentation broth; entering the treated fermentation broth into a wastewater treatment system, or into a wastewater treatment system after being treated according to a conventional process in the art, or combining the treated fermentation broth with other wastewater produced in another process for producing a long chain dicarboxylic acid and entering into a wastewater treatment system, wherein the liquid that enters a wastewater treatment system is called wastewater.

In a preferred embodiment of the present invention, the salt in the wastewater comprises, but not limited to, one or more of potassium salt, sodium salt, magnesium salt, calcium salt, iron salt, ammonium salt, hydrochloride, carbonate, sulfate, nitrate and phosphate. The salt in the treated fermentation broth of a long chain dicarboxylic acid comprises an inorganic salt, and may also comprise very few soluble salts of the long chain dicarboxylic acid.

Specifically, the salt content may be 12000 ppm, 11000 ppm, 10000 ppm, 9000 ppm, 8000 ppm, 7000 ppm, 6000 ppm, 5000 ppm, 4000 ppm, 3000 ppm, 2000 ppm, or 1000 ppm.

In a preferred embodiment of the present invention, the total amount of the inorganic ions in the wastewater is below 7000 ppm.

Still yet another object of the present invention is a method for preparing a long chain dicarboxylic acid, comprising the following steps:

(1) obtaining a fermentation broth of a long chain dicarboxylic acid according to the method for producing a long chain dicarboxylic acid by fermentation as mentioned above;

(2) acidifying the fermentation broth obtained in step (1) to obtain a solid and a treated fermentation broth, separating and then dissolving the solid in an organic solvent, and separating and crystallizing the supernatant to obtain a product of the long chain dicarboxylic acid.

In a preferred embodiment of the present invention, the treated fermentation broth is a mixed solution obtained after removing the solid in the fermentation broth. The solid comprises particles of the long chain dicarboxylic acid; alternatively, the solid comprises particles of the long chain dicarboxylic acid and cells. The treated fermentation broth may or not comprise a cell.

In a preferred embodiment of the present invention, the salt content in the treated fermentation broth is controlled to be below 12000 ppm by acidification, and the parts per million is the parts per million by mass of the salt to the treated fermentation broth of the long chain dicarboxylic acid.

In a preferred embodiment of the present invention, the salt in the treated fermentation broth of a long chain dicarboxylic acid comprises, but not limited to, one or more of potassium salt, sodium salt, magnesium salt, calcium salt, iron salt, ammonium salt, hydrochloride, carbonate, sulfate, nitrate and phosphate. The salt in the treated fermentation broth of a long chain dicarboxylic acid comprises an inorganic salt, and may also comprise very few soluble salt of the long chain dicarboxylic acid.

Specifically, the salt content in the treated fermentation broth may be 12000 ppm, 11000 ppm, 10000 ppm, 9000 ppm, 8000 ppm, 7000 ppm, 6000 ppm, 5000 ppm, 4000 ppm, 3000 ppm, 2000 ppm, or 1000 ppm.

In a preferred embodiment of the present invention, the salt content in the treated fermentation broth is below 7000 ppm.

In a preferred embodiment of the present invention, the salt in the treated fermentation broth comprises an inorganic salt. The inorganic salt accounts for the majority of the total salts. The salt in the treated fermentation broth may also comprise a salt of the dicarboxylic acid. The salt of the dicarboxylic acid accounts for very little of the total salts.

In a preferred embodiment of the present invention, the pH of the acidification is preferably from 2.5 to 5, and more preferably from 3 to 4, and may be 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

In a preferred embodiment of the present invention, the acidification is performed by using sulfuric acid and/or hydrochloric acid.

In a preferred embodiment of the present invention, the method for separating is centrifugation or filtration.

In a preferred embodiment of the present invention, the organic solvent comprises one or more of alcohols, acids, ketones and esters. Among them, the alcohol comprises one or more of methanol, ethanol, isopropanol and n-butanol. The acid comprises acetic acid. The ketone comprises acetone. The ester comprises ethyl acetate and/or butyl acetate.

In a preferred embodiment of the present invention, a supernatant is obtained by decolorization and then separation after the solid is dissolved in an organic solvent. The method for decolorization may be activated carbon decolorization. The amount of the added activated carbon is no more than 5% of the volume of the supernatant. The temperature of the decolorization is from 85 to 100° C. The decolorization time is from 15 to 165 min.

In a preferred embodiment of the present invention, the crystallization is cooling crystallization. The cooling crystallization includes the following steps: cooling down to from 65 to 80° C. and keeping for 1 to 2 hours, then cooling down to from 25 to 35° C., and crystallizing.

In a preferred embodiment of the present invention, a product of dicarboxylic acid is obtained by separation after crystallization. The method for separation is centrifugation.

The method for producing a long chain dicarboxylic acid provided by the present invention can effectively reduce the amount of alkali used in the fermentation process, and can also remarkably reduce the amount of acid used in the subsequent extraction of the long chain dicarboxylic acid, thereby reducing the total amount of salts in the wastewater produced in the production process of the long chain dicarboxylic acid. In addition, the production method of the present invention also has many advantages such as shortening the fermentation time, increasing the acid production, reducing the amount of medium, and suitable for the production of various types of long-chain dicarboxylic acids, etc. Compared with the existing production processes, the method of the present invention not only has significant cost advantages, but also can effectively reduce the pressure on resource and environment, thus it has a very obvious value advantage in industrialization.

DETAILED DESCRIPTION OF THE EMBODIMENTS

A method for producing a long chain dicarboxylic acid by fermentation, wherein the content of salt in the fermentation broth of the fermentation is below 20%, preferably below 15%, and more preferably below 10%, and may specifically be 20%, 19%, 18%, 17%, 16%, 15%, 14%, 13%, 12%, 11%, 10%, 9%, 8%, 7%, 6%, 5%, 4%, 3%, 2%, or 1%, wherein the percentage is a mass percentage relative to the total amount of the long chain dicarboxylic acid produced by fermentation; and the salt comprises, but not limited to, one or more of potassium salt, sodium salt, magnesium salt, calcium salt, sulfate, nitrate and phosphate.

In the method for producing a long chain dicarboxylic acid by fermentation of the present invention, the fermentation process comprises trophophase and conversion phase (acid-producing phase).

In a preferred embodiment according to the production method of a long chain dicarboxylic acid of the present invention, the pH during the trophophase of the fermentation is above 3.0, preferably from 3.5 to 6.5, and may specifically be 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0.

In a preferred embodiment according to the method for producing a long chain dicarboxylic acid by fermentation of the present invention, the pH during the conversion phase of the fermentation is below 7.0, preferably from 4.0 to 6.8, and more preferably from 5.0 to 6.5; and may specifically be 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0.

In a preferred embodiment according to the method for producing a long chain dicarboxylic acid by fermentation of the present invention, the pH of the fermentation system is controlled to be below 7.0, preferably from 4.0 to 6.8, and more preferably from 5.0 to 6.5, when the optical cell density ($OD_{620}$) is above 0.5 (diluted 30 times) during the fermentation.

The method for adjusting or controlling pH value according to the present invention is not particularly limited, and it may be a combination of one or more manners of controlling constant at a certain pH value, not controlling pH value, controlling pH not below a certain pH value, controlling pH not above a certain pH value, adjusting pH value up, adjusting pH value down, controlling pH to fall or naturally to fall within a pH range from outside the pH range.

In the present invention, the fermentation is performed under an acidic condition, so that the amount of alkali added in the fermentation process is greatly reduced, and the salt content in the fermentation broth, the treated fermentation broth and the wastewater is greatly reduced. At the same time, the present invention can also ensure good fermentation conversion rate and higher acid production under the above pH conditions.

In a preferred embodiment of the method for producing a long chain dicarboxylic acid by fermentation according to the present invention, the temperature of the fermentation is between 28 and 32° C.

In a preferred embodiment of the method for producing a long chain dicarboxylic acid by fermentation according to the present invention, the aeration rate of the fermentation is between 0.3 and 0.7 vvm.

In a preferred embodiment of the method for producing a long chain dicarboxylic acid by fermentation according to the present invention, the pressure of the fermentation is between 0.05 and 0.14 MPa.

In a preferred embodiment of the method for producing a long chain dicarboxylic acid by fermentation according to the present invention, the dissolved oxygen in the conversion process of the fermentation is not less than 15%.

In a preferred embodiment of the method for producing a long chain dicarboxylic acid by fermentation according to the present invention, 0% to 3% alkane is added at the start of the fermentation.

In a preferred embodiment of the method for producing a long chain dicarboxylic acid by fermentation according to the present invention, the inoculum amount of the fermentation is between 10% and 30%.

In a preferred embodiment of the method for producing a long chain dicarboxylic acid by fermentation according to the present invention, a substrate is added for fermentation conversion when the strain is cultured to a cell optical density ($OD_{620}$) of above 0.5 (diluted 30 times).

In a preferred embodiment of the method for producing a long chain dicarboxylic acid by fermentation according to the present invention, the strain for fermentation comprises *Candida tropicalis* or *Candida sake*, preferably *Candida tropicalis* (Deposit No. CCTCC M203052), or *Candida tropicalis* CATN145 (Deposit No. CCTCC M 2011192), or *Candida sake* CATH4013 (Deposit No. CCTCC M2011486), or *Candida tropicalis* CAT H1614 (Deposit No. CCTCC M 2013143), or *Candida sake* CATH4014 (Deposit No. CCTCC M2011487), or *Candida sake* CATH4012 (Deposit No. CCTCC M2011485), or *Candida sake* CATH4016 (Deposit No. CCTCC M2011488), or *Candida sake* CATH430 (Deposit No. CCTCC M2011489).

The ingredients in the fermentation medium may comprise a carbon source, a nitrogen source, an inorganic salt, a nutritional factor, and so on. Among them, the carbon source may be a fermentable sugar by *Candida*, comprising one or more of glucose, sucrose and maltose, etc.; the nitrogen source may be an organic nitrogen and/or an inorganic nitrogen, and the organic nitrogen comprises one or more of yeast extract, peptone and corn steep liquor, and the inorganic nitrogen comprises one or more of urea, ammonium sulfate and potassium nitrate; the inorganic salt comprises one or more of potassium dihydrogen phosphate, potassium chloride, magnesium sulfate, calcium chloride, ferric chloride and copper sulfate; and the nutritional factor comprises one or more of vitamin B1, vitamin B2, vitamin C and biotin.

The "YPD medium" used in the production method of the present invention comprises the following ingredients: glucose 2%, yeast extract 1%, and peptone 2%.

The "seed medium" used in the production method of the present invention is a medium required for preparing a seed of the microorganism. A microbial strain is inoculated into a seed medium and cultured under a certain condition. After the seed culture is mature, it can be used as a seed required for further scale-up culture and fermentation. The seed medium used in the Examples of the present invention is an aqueous medium comprising the following ingredients: sucrose 1% to 3%, corn steep liquor 0.15% to 1%, yeast extract 0.2% to 1.5%, $KH_2PO_4$ 0.4% to 1.5%, and urea 0.05% to 0.5% (w/v).

In a preferred embodiment of the method for producing a long chain dicarboxylic acid by fermentation according to the present invention, an aqueous medium (hereinafter abbreviated as "fermentation medium 1") can be used, comprising the following ingredients: glucose 1% to 5%, corn steep liquor 0.1% to 0.9%, yeast extract 0.1% to 0.5%, potassium nitrate 0.05% to 1.2%, potassium dihydrogen phosphate 0.05% to 1.0%, urea 0.05% to 0.3%, ammonium sulfate 0.05% to 0.3%, and sodium chloride 0.05% to 0.2% (w/v). Fermentation medium 1 can be suitable for the fermentation production in a scale from a shake flask of tens of milliliters to a fermenter of hundreds of tons.

In a preferred embodiment of the method for producing a long chain dicarboxylic acid by fermentation according to the present invention, an aqueous medium (hereinafter abbreviated as "fermentation medium 2") with nutrients of low concentrations can be used, comprising the following ingredients: glucose 1% to 5%, potassium nitrate 0.05% to 0.6%, potassium dihydrogen phosphate 0.02% to 0.6%, ammonium sulfate 0.05% to 0.3% and magnesium sulfate 0.05% to 0.3% (w/v). Some complex ingredients such as corn steep liquor, yeast extract, etc. are lacked in the fermentation medium. The composition of the medium is more definite, and the fermentation index and product quality can be controlled better. It can be constituted with water, sterilized at 121° C. for 20 min, cooled to a suitable temperature, and used in a fermentation culture.

In a preferred embodiment of the method for producing a long chain dicarboxylic acid by fermentation according to the present invention, the conversion rate of fermentation can be further increased by feeding an aqueous sugar solution as carbon source during the conversion of the fermentation. The aqueous sugar solution can be fed in batch or continuous mode. The sugar may be common sucrose or glucose, and the concentration of the fed aqueous sugar solution may be from 10% to 70% (w/v). The sugar concentration in the fermentation conversion system is controlled to be between 0.1% and 1% (w/v) by feeding an aqueous sugar solution.

In a preferred embodiment of the method for producing a long chain dicarboxylic acid by fermentation according to the present invention, the substrate for the fermentation comprises an alkane, preferably C9 to C22 normal alkane, more preferably C9 to C18 normal alkane, and most preferably C10, C11, C12, C13, C14, C15 or C16 normal alkane.

In a preferred embodiment of the method for producing a long chain dicarboxylic acid by fermentation according to the present invention, the long chain dicarboxylic acid comprises C9 to C22 long chain dicarboxylic acid, preferably C9 to C18 long chain dicarboxylic acid, and more preferably one or more of sebacic acid, undecanedioic acid, dodecanedioic acid, brassylic acid, tetradecanedioic acid, pentadecanedioic acid and hexadecanedioic acid.

The present invention further provides a fermentation broth of a long chain dicarboxylic acid obtained from the above fermentation method. The salt content in the fermentation broth is below 20%, preferably below 15%, and more preferably below 10%, and may specifically be 20%, 19%, 18%, 17%, 16%, 15%, 14%, 13%, 12%, 11%, 10%, 9%, 8%, 7%, 6%, 5%, 4%, 3%, 2% and 1%, wherein the percentage is a mass percentage relative to the total amount of the long chain dicarboxylic acid produced by fermentation.

The fermentation broth is a fermentation broth obtained by fermentation under an acidic condition. In the fermentation process or after completion of the fermentation, most of long chain dicarboxylic acids are precipitated in a crystal form or an amorphous form of long chain dicarboxylic acids, very few are precipitated in the form of salts of long chain dicarboxylic acids, and very few long chain dicarboxylic acids dissolve in the fermentation broth in the form of salts thereof.

A treated fermentation broth is obtained by removing a solid in the above fermentation broth. The means to remove a solid may be acidification.

The solid according to the present invention comprises a particle of the long chain dicarboxylic acid; alternatively, comprises a particle of the long chain dicarboxylic acid and a cell. That is: the treated fermentation broth may or not comprise a cell. The particle of the long chain dicarboxylic acid according to the present invention comprises a large amount of crystals of long chain dicarboxylic acids as well as long chain dicarboxylic acids in an amorphous form, and may also comprise very few solids of long chain dicarboxylic acids present in the form of salts, etc.

In the treated fermentation broth according to the present invention, the salt content is below 12000 ppm, and the parts per million is the parts per million by mass of the salt to the treated fermentation broth of the long chain dicarboxylic acid. The salt comprise, but not limited to, one or more of potassium salt, sodium salt, magnesium salt, calcium salt, iron salt, ammonium salt, hydrochloride, carbonate, sulfate, nitrate and phosphate. The salt in the treated fermentation broth of a long chain dicarboxylic acid comprises an inorganic salt, and may also comprise very few soluble salts of the long chain dicarboxylic acid.

Specifically, the salt content may be 12000 ppm, 11000 ppm, 10000 ppm, 9000 ppm, 8000 ppm, 7000 ppm, 6000 ppm, 5000 ppm, 4000 ppm, 3000 ppm, 2000 ppm, or 1000 ppm.

In a preferred embodiment of the production method of a long chain dicarboxylic acid according to the present invention, the total amount of inorganic ions in the treated fermentation broth is below 7000 ppm.

The present invention further provides a wastewater produced by a method for producing a long chain dicarboxylic acid by fermentation, wherein the salt content is below 12000 ppm, and the parts per million is the parts per million by mass of the inorganic salt to the wastewater. The wastewater is a liquid that enters a wastewater treatment system, obtained by removing a solid in the above fermentation broth of a long chain dicarboxylic acid. Specifically, the fermentation broth is acidified to obtain a solid and a treated fermentation broth; the solid comprises a particle of the long chain dicarboxylic acid, and may further comprise a cell; that is, the treated fermentation broth may or not comprise a cell. The treated fermentation broth enters a wastewater treatment system, or enters a wastewater treatment system after being treated according to a conventional process in the art, and the liquid that enters a wastewater treatment system is called wastewater.

Specifically, the content of an inorganic salt may be 12000 ppm, 11000 ppm, 10000 ppm, 9000 ppm, 8000 ppm, 7000 ppm, 6000 ppm, 5000 ppm, 4000 ppm, 3000 ppm, 2000 ppm, or 1000 ppm.

In a preferred embodiment of the production method of a long chain dicarboxylic acid according to the present invention, the total amount of inorganic ions in the wastewater is below 7000 ppm.

The present invention further provides a method for preparing a long chain dicarboxylic acid, comprising the following steps:

(1) obtaining a fermentation broth of a long chain dicarboxylic acid according to the above method for producing a long chain dicarboxylic acid by fermentation;

(2) acidifying the fermentation broth obtained in step (1) to obtain a solid and a treated fermentation broth, and separating and then dissolving the solid in an organic solvent, and obtaining a supernatant by separation and crystallizing to obtain a product of the long chain dicarboxylic acid.

In a preferred embodiment of the preparation method of a long chain dicarboxylic acid according to the present invention, the salt content in the treated fermentation broth is controlled to be below 12000 ppm by acidification, and the parts per million is the parts per million by mass of the salt to the treated fermentation broth of the long chain dicarboxylic acid.

In a preferred embodiment of the preparation method of a long chain dicarboxylic acid according to the present invention, the treated fermentation broth is a mixed solution obtained after removing a solid in the fermentation broth. The solid comprises a particle of the long chain dicarboxylic acid; alternatively, the solid comprises a particle of the long chain dicarboxylic acid and a cell. The treated fermentation broth may or not comprise a cell.

In a preferred embodiment of the method of preparing a long chain dicarboxylic acid according to the present invention, the pH of the acidification is preferably between 2.5 and 5, more preferably between 3 and 4, and may be 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0.

In a preferred embodiment of the preparation method of a long chain dicarboxylic acid according to the present invention, the acidification is performed by using sulfuric acid and/or hydrochloric acid.

In a preferred embodiment of the method of preparing a long chain dicarboxylic acid according to the present invention, the method for separation is centrifugation or filtration.

In a preferred embodiment of the method of preparing a long chain dicarboxylic acid according to the present invention, the organic solvent comprises one or more of alcohols, acids, ketones and esters. Among them, the alcohol comprises one or more of methanol, ethanol, isopropanol and n-butanol. The acid comprises acetic acid. The ketone comprises acetone. The ester comprises ethyl acetate and/or butyl acetate.

In a preferred embodiment of the method of preparing a long chain dicarboxylic acid according to the present invention, a supernatant is obtained by decolorization and separation after the solid is dissolved in an organic solvent. The method for decolorization may be activated carbon decolorization. The amount of the added activated carbon is no more than 5% of the volume of the supernatant. The temperature of the decolorization is from 85 to 100° C. The decolorization time is between 15 and 165 min.

In a preferred embodiment of the method of preparing a long chain dicarboxylic acid according to the present invention, the crystallization is cooling crystallization. The cooling crystallization comprises the following steps: cooling down to between 65 and 80° C., and keeping for 1 to 2 hours, then cooling down to between 25 and 35° C., and crystallizing.

In a preferred embodiment of the method of preparing a long chain dicarboxylic acid according to the present invention, a product of the dicarboxylic acid is obtained by separation after crystallization. The method for separation is centrifugation.

In a preferred embodiment of the method of producing a long chain dicarboxylic acid according to the present invention, the production process of a long chain dicarboxylic acid comprises:

Cultivation Process of Seed Flask:

A tube of *Candida tropicalis* strain in glycerol is inoculated into a seed flask containing YPD medium, and the pH is natural. The culture is cultivated in a shaker at from 28 to 32° C. and from 200 to 250 rpm for 1 to 2 days.

Cultivation Process of Seed Tank:

A seed in shake flask is inoculated into a seed tank containing seed medium, and the inoculum amount is from 10% to 30%. The initial pH value of the fermentation system after inoculation is from 6.0 to 6.8. The culture is cultivated for 15 to 30 hours at 28 to 32° C., with an aeration rate of 0.3 to 0.7 vvm and a tank pressure of 0.05 to 0.14 MPa. A certain agitation rate is maintained and DO in the fermentation process of the seed is controlled to be not below 10%. The criteria of a mature seed culture are that $OD_{620}$ after diluted 30 times is above 0.5, more preferably between 0.5 and 1.0.

Fermentation Process:

The seed broth obtained in seed tank culture is inoculated into a fermenter containing a fermentation medium, and the initial volume is 4 to 6 L after inoculation and the inoculum amount is 10% to 30% (v/v, relative to the initial volume of the fermentation). 0-10% (v/v, relative to the initial volume of the fermentation, hereinafter the same) of an alkane is added at the start of the fermentation. A temperature of from 28 to 32° C., an aeration rate of about 0.3 to 0.7 vvm, and a tank pressure (gauge pressure) of about 0.05 to 0.14 MPa are controlled during the fermentation. A certain agitation rate is maintained, and the dissolved oxygen is controlled to be not below 10%. The pH value of the fermentation broth is controlled, and the pH is about 5.0 to 6.8 at the start of the fermentation; the pH of the fermentation broth gradually decreases with the growth of the microorganism, and the pH is controlled to be not below 3.0; and when the optical cell density ($OD_{620}$) is above 0.5 (diluted 30 times), the pH is controlled to be from 4.0 to 6.8, more preferably from 5.0 to 6.5 until the end of the fermentation. An alkane is fed in batch when the fermentation period is 10 to 20 hours, and the alkane content in the fermentation broth is controlled to be not above 10%, and the total fermentation period is about 100 to 180 hours. Alternatively, the concentration of sugar in the fermentation broth is controlled to be 0.1% to 1% (w/v) by feeding an aqueous sugar solution during the fermentation.

Extraction Process:

The fermentation broth is acidified to obtain a solid and a treated fermentation broth, and the solid is separated and then dissolved in an organic solvent, and a supernatant is obtained by separation and crystallized to obtain a product of the long chain dicarboxylic acid.

The long chain dicarboxylic acid according to the present invention comprises a dicarboxylic acid with a chemical formula $HOOC(CH_2)nCOOH$, wherein n≥7, preferably 20≥n≥7, more preferably 16≥n≥7. Examples of LCDA according to the present invention comprise: azelaic acid ($HOOC(CH_2)_7COOH$), sebacic acid ($HOOC(CH_2)_8COOH$), undecanedioic acid ($HOOC(CH_2)_9COOH$, 1,9-nonanedicarboxylic acid or 1,11-undecanedioic acid, and referenced herein as "DC11"), dodecanedioic acid ($HOOC(CH_2)_{10}COOH$, 1,10-decanedicarboxylic acid or 1,12-dodecanedioic acid, and referenced herein as "DC12"), brassylic acid ($HOOC(CH_2)_{11}COOH$, 1,11-undecanedicarboxylic acid or 1,13-tridecanedioic acid, and referenced herein as "DC13"), tetradecanedioic acid ($HOOC(CH_2)_{12}COOH$, 1,12-dodecanedicarboxylic acid or 1,14-tetradecanedioic acid, and referenced herein as "DC14"), pentadecanedioic acid ($HOOC(CH_2)_{13}COOH$, 1,13-tridecanedicarboxylic acid or 1,15-pentadecanedioic acid, and referenced herein as "DC15"), hexadecanedioic acid ($HOOC(CH_2)_{14}COOH$, 1,14-tetradecanedicarboxylic acid or 1,16-hexadecanedioic acid, and referenced herein as "DC16"), heptadecanedioic acid ($HOOC(CH_2)_{15}COOH$, 1,15-pentadecanedicarboxylic acid or 1,17-heptadecanedioic acid, and referenced herein as "DC17"), and octadecanedioic acid ($HOOC(CH_2)_{16}COOH$, 1,16-hexadecanedicarboxylic acid or 1,18-octadecanedioic acid, and referenced herein as "DC18"), etc.

In some examples of the method of producing a long chain dicarboxylic acid according to the present invention, an acid production of at least 110 mg/g of undecanedioic acid, at least 150 mg/g of dodecanedioic acid, at least 130 mg/g of brassylic acid, at least 150 mg/g of tetradecanedioic acid, at least 140 mg/g of pentadecanedioic acid, or at least 130 mg/g of hexadecanedioic acid can be achieved in a fermentation process of 10 L fermenter.

In some examples of the method of producing a long chain dicarboxylic acid according to the present invention, compared with a traditional process, at least 60% of the alkali usage can be saved in a fermentation process of 10 L fermenter; in some other examples, about 90% of the alkali usage can be saved.

In some examples of the method of producing a long chain dicarboxylic acid according to the present invention, the salt content in the treated fermentation broth can be lowered to 6000 ppm.

In some examples of the method of producing a long chain dicarboxylic acid according to the present invention, an acid production of at least 150 mg/g of dodecanedioic acid can be achieved and a conversion rate by weight of above 92% (w/w, weight percentage of an alkane that is converted to a dicarboxylic acid) is reached in a fermentation process of 200 $M^3$ fermenter.

In some examples of the method of producing a long chain dicarboxylic acid according to the present invention, the conversion rate of fermentation can be increased by feeding a secondary carbon source, and a conversion rate by weight of above 95% (w/w, weight percentage of an alkane that is converted to a dicarboxylic acid) is reached.

In some examples of the method of producing a long chain dicarboxylic acid according to the present invention, an acid production of at least 140 mg/g of brassylic acid can be achieved and a conversion rate by weight of above 85% (w/w, weight percentage of an alkane that is converted to a dicarboxylic acid) is reached in a fermentation process of 200 $M^3$ fermenter.

In some examples of the method of producing a long chain dicarboxylic acid according to the present invention, an acid production of at least 150 mg/g of dodecanedioic acid can be achieved and a conversion rate by weight of above 90% (w/w, weight percentage of an alkane that is converted to a dicarboxylic acid) is reached in a fermentation process of 450 $M^3$ fermenter.

The present invention is hereinafter described in detail by the examples to make the features and advantages of the present invention clear. However, it should be noted that the examples are intended to explain the concepts of the present invention, and the scope of the present invention is not limited only to the examples listed herein.

The Examples of the present invention employed the techniques well known to those skilled in the art, for example, the concentration of dicarboxylic acid in the fermentation broth is determined using determination methods disclosed in Chinese Patent No. ZL 95117436.3. Specifically, the determination process includes: adjusting the pH of the fermentation broth to pH 3.0 with hydrochloric acid solution, and then adding 100 mL of ether to extract the dicarboxylic acid in the fermentation broth; removing the ether by evaporation to obtain a powder of a dicarboxylic acid; and dissolving the obtained powder of a dicarboxylic acid in ethanol and titrating with a NaOH solution of 0.1 mol/L to finally determine the titer of the dicarboxylic acid in the fermentation broth.

The method of determining the salt content in the fermentation broth in the Examples of the present invention includes: centrifuging or filtering the fermentation broth to obtain a supernatant, and placing the supernatant in a glass evaporating dish which is dried to constant weight to dryness in a water bath. If the residue has a color, hydrogen peroxide is added dropwise until the bubbles disappear, and then the solution is evaporated to dryness in a water bath, and the process is repeated several times until the color turns white or the color remains unchanged. The dried evaporating dish is dried to constant weight and weighted; and the salt content is calculated.

The method of determining the salt content in the treated fermentation broth in the Examples of the present invention includes: placing the treated fermentation broth in a glass evaporating dish being dried to constant weight and evaporated to dryness in a water bath; if the residue has a color, hydrogen peroxide is added dropwise until the bubbles disappear, and then solution is evaporated to dryness in a water bath, and the process is repeated several times until the color turns white or the color remains unchanged; the evaporated evaporating dish is dried to constant weight and weighted; and the salt content is calculated.

The method of determining the salt content in the wastewater in the Examples of the present invention includes: placing the wastewater sample in a glass evaporating dish being dried to constant weight and evaporated to dryness in a water bath; if the residue has a color, hydrogen peroxide is added dropwise until the bubbles disappear, and then the solution is evaporated to dryness in a water bath, and the process is repeated several times until the color turns white or the color remains unchanged; the evaporated evaporating dish is dried to constant weight and weighted; and the salt content is calculated.

was inoculated into a seed tank containing 5 L seed medium (sucrose 2%, corn steep liquor 0.3%, yeast extract 0.5%, $KH_2PO_4$ 0.8%, and urea 0.3%), and the inoculum amount was 10%. The initial pH value of the system after inoculation was 6.0. The culture was cultivated for 18 h at 29° C., with an aeration rate of 0.4 vvm and a tank pressure of 0.08 MPa. The pH naturally decreased to 3 during the culturing. When $OD_{620}$ was 0.7, the seed broth was inoculated into a fermenter containing 6 L fermentation medium 1 (glucose 4%, corn steep liquor 0.5%, yeast extract 0.4%, potassium nitrate 1%, potassium dihydrogen phosphate 0.1%, urea 0.12%, ammonium sulfate 0.06%, and sodium chloride 0.1%), and the initial volume was 5 L after inoculation and the inoculum amount was 20%. A temperature of 30° C., an aeration rate of about 0.4 vvm, and a tank pressure (gauge pressure) of about 0.12 MPa were controlled, and dissolved oxygen was controlled to be not below 20% in the fermentation process. The pH value of the fermentation broth was controlled by feeding 30% liquid alkali. Cells mainly grew at prophase of fermentation. The pH was about 6.5 at the start of the fermentation; the pH of the fermentation broth gradually decreased with the growth of the microorganism, and the pH was controlled to be not below 3.0; and the pH was controlled to be about 5.0 when the optical cell density ($OD_{620}$) was greater than 0.5 (diluted 30 times) until the end of the fermentation. The alkane was fed in batch when the fermentation period was 10 to 20 hours, and the alkane content in the fermentation broth was controlled to be not above 10%.

Examples 1~6 are, respectively, fermenting undecane (Example 1), dodecane (Example 2), tridecane (Example 3), tetradecane (Example 4), pentadecane (Example 5), and hexadecane (Example 6) to prepare corresponding long chain dicarboxylic acids according to the above fermentation process.

The obtained fermentation broth was acidified and crystallized according to conventional methods in the art to remove cells and a long chain dicarboxylic acid to obtain a treated fermentation broth.

Results of acid productions of different long chain dicarboxylic acids and salt contents in their fermentation broths and treated fermentation broths are shown in Table 1.

TABLE 1

Results of acid productions of different long chain dicarboxylic acids and salt contents in their fermentation broths and treated fermentation broths

| Process | Raw material | Long chain dicarboxylic acid | Fermentation period/h | Acid production/ mg/g | Alkali consumption/mL | Salt content in fermentation broths/% | Salt content in treated fermentation broths/ppm |
|---|---|---|---|---|---|---|---|
| Example 1 | C11 alkane | DC11 | 151 | 110.4 | 90 | 9.71 | 6500 |
| Example 2 | C12 alkane | DC12 | 132 | 152.6 | 85 | 7.94 | 6300 |
| Example 3 | C13 alkane | DC13 | 135 | 137.2 | 93 | 8.85 | 6600 |
| Example 4 | C14 alkane | DC14 | 128 | 155.1 | 102 | 8.0 | 6700 |
| Example 5 | C15 alkane | DC15 | 136 | 143.1 | 115 | 8.96 | 6900 |
| Example 6 | C16 alkane | DC16 | 148 | 134.8 | 105 | 8.87 | 6700 |

Examples 1~6: Production of Various Dicarboxylic Acids by Fermentation of *Candida tropicalis* CAT H1614 in a 10 L Fermenter A tube of *Candida tropicalis* CAT H1614 strain in glycerol was inoculated into a seed flask containing 30 ml YPD liquid medium (glucose 2%, yeast extract 1%, and peptone 2%), and the pH is natural. The culture was cultivated in a shaker at 29° C. and 220 rpm for 1 day. A seed in shake flask Among them, the salt content in the fermentation broth is a mass percentage relative to the total amount of the long chain dicarboxylic acid produced by fermentation.

The salt content in the treated fermentation broth is parts per million by mass of the salt to the treated fermentation broth of the long chain dicarboxylic acid.

As can be seen from the results in Table 1, the present invention ferments a long chain alkane under an acidic condition to prepare a corresponding long chain dicarboxylic acid with high production, and salt contents in fermentation broth and treated fermentation broth are low.

Example 7: Production of a Long Chain Dicarboxylic Acid by Fermentation of *Candida tropicalis* CAT H1614 in a 10 L Fermenter DC12 was fermented by the process of the present invention: A tube of *Candida tropicalis* CAT H1614 strain in glycerol was inoculated into a seed flask containing 25 ml YPD liquid medium (glucose 2%, yeast extract 1%, and peptone 2%), and the pH was natural. The culture was cultivated in a shaker at 30° C. and 230 rpm for 2 days. A seed in shake flask was inoculated into a 10 L seed tank containing 6 L seed medium (sucrose 2%, corn steep liquor 0.3%, yeast extract 0.5%, $KH_2PO_4$ 0.8%, and urea 0.3%), and the inoculum amount was 20%. The initial pH value of the system after inoculation was 6.2. The culture was cultivated for 20 h at 30° C., with an aeration rate of 0.5 vvm and a tank pressure of 0.1 MPa. The pH naturally decreased to 3 during the culture. When $OD_{620}$ was 0.6, the seed broth was inoculated into a fermenter containing fermentation medium 1 (glucose 2%, corn steep liquor 0.2%, yeast extract 0.2%, potassium nitrate 0.08%, potassium dihydrogen phosphate 0.3%, urea 0.2%, ammonium sulfate 0.1%, and sodium chloride 0.1%), and the initial volume was 6 L after inoculation and the inoculum amount was 15%. 6% dodecane was added at the start of the fermentation. A temperature of 28° C., an aeration rate of about 0.4 vvm, and a tank pressure (gauge pressure) of about 0.11 MPa were controlled, and dissolved oxygen was controlled to be not below 20% in the fermentation process. The pH value of the fermentation broth was controlled by feeding 32% liquid alkali. Cells mainly grew at prophase of fermentation, and the pH was about 6.6 at the start of the fermentation; the pH of the fermentation broth gradually decreased with the growth of the microorganism, and the pH was controlled to be not below 3.0; and the pH was controlled to be pH5.5 when the optical cell density ($OD_{620}$) was greater than 0.5 (diluted 30 times) until the end of the fermentation. The alkane was fed in batch when the fermentation period was 10 to 20 hours, and the alkane content in the fermentation broth was controlled to be not above 10%.

Comparative Example 1: Production of a Long Chain Dicarboxylic Acid by Fermentation of *Candida tropicalis* CAT H1614 in a 10 L Fermenter Using Traditional Process DC12 was fermented by the original traditional process: A tube of *Candida tropicalis* CAT H1614 strain in glycerol was inoculated into a seed flask containing 25 ml YPD medium, and the pH was natural. The culture was cultivated in a shaker at 30° C. and 230 rpm for 2 days. A seed in shake flask was inoculated into a 10 L seed tank containing 6 L seed medium (sucrose 2%, corn steep liquor 0.3%, yeast extract 0.5%, $KH_2PO_4$ 0.8%, and urea 0.3%), and the inoculum amount was 20%. The initial pH value of the system after inoculation was 6.2. The culture was cultivated for 20 h at 30° C., with an aeration rate of 0.5 vvm and a tank pressure of 0.1 MPa. The pH naturally decreased to 3 during the culturing. When $OD_{620}$ was 0.6, the seed broth was inoculated into a fermenter containing fermentation medium (glucose 3%, potassium dihydrogen phosphate 0.5%, yeast extract 0.2%, corn steep liquor 0.15%, urea 0.25%, sodium chloride 0.2%, and potassium nitrate 0.7%). The C12 alkane and feeding sugar were sterilized separately. The culture was cultivated under the conditions of: 29° C., an aeration rate of 0.5 vvm, and a tank pressure of 0.1 MPa. The pH was natural during the first 20 hours of the fermentation, and cells mainly grew. When the optical cell density ($OD_{620}$) was above 0.6, a C12 alkane was fed in batch; after that, feeding every 8 hours to control the concentration of an alkane in the fermentation broth to be about 5% (V/V); at the same time, the pH was adjusted to 6.5; after 48 hours, the pH was adjusted to 7.0 by using NaOH solution every 4 hours; 48 to 72 hours, the pH was adjusted to 7.5 by using NaOH solution every 4 hours; 72 to 120 hours, the pH was adjusted to 7.8 by using NaOH solution every 4 hours; from 120 hours to harvesting fermentation broth, the pH was adjusted to 8.0 by using NaOH solution every 4 hours. 1% (W:V) glucose was fed in batch at 24, 48 and 72 hours in the fermentation.

TABLE 2

Results of fermentation by different processes

| Group | Process | Acid production mg/g | Period/ h | Conversion rate | Alkali addition/ mL |
|---|---|---|---|---|---|
| Example 7 | Process of the present invention | 165 | 135 | 92% | 95 |
| Comparative Example 1 | Traditional process | 118 | 170 | 75% | 954 |

The fermentation broths of Example 7 and Comparative Example 1 were acidified and crystallized according to conventional methods in the art to remove cells and a long chain dicarboxylic acid to obtain treated fermentation broths. According to the determination methods as mentioned above, the salt contents in the fermentation broths and treated fermentation broths are shown in Table 3.

TABLE 3

Salt contents in fermentation broths and treated fermentation broths by different fermentation processes

| Process | Salt content in the fermentation broth (%) | Salt content in the treated fermentation broth (ppm) |
|---|---|---|
| Example 7 | 8.8 | 6500 |
| Comparative Example 1 | / | 68750 |

The salt in the fermentation broth in Example 7 was mainly an inorganic salt, whose content is very low relative to a long chain dicarboxylic acid; and the salt in the fermentation broth in Comparative Example 1 was mainly a salt of a long chain dicarboxylic acid, whose amount was above 100% relative to a long chain dicarboxylic acid. As a long chain dicarboxylic acid was desired, acidification and crystallization had to be performed, and a large amount of inorganic salts was required to be added, resulting in the salt content in the treated fermentation broth far more than that of the present invention. The salt content in the fermentation broth was a mass percentage relative to a long chain dicarboxylic acid.

The salt content in the treated fermentation broth was parts per million by mass of the salt to the treated fermentation broth of the long chain dicarboxylic acid.

As can be seen from the results in Table 3, the salt content in the fermentation broth and treated fermentation broth obtained by the fermentation under an acidic condition of the present invention reduces obviously, which can significantly reduce the requirements of the subsequent purification process, thereby bringing a reduction in production cost and pressure on environment.

Example 8: Fermentation of DC12 with *Candida tropicalis* CAT H1614 in a 200 M³ Fermenter A tube of the strain in glycerol was inoculated into a seed flask containing seed medium, and the pH was natural. The culture was cultivated in a shaker at 28° C. and 230 rpm for 2 days. A seed in shake flask was inoculated into a seed tank containing seed medium, and the inoculum amount was 10%. The initial pH value of the system after inoculation was 6.3. The culture was cultivated for 25 h at 28° C., with an aeration rate of 0.6 vvm and a tank pressure of 0.11 MPa. The pH naturally decreased to 3 during the culture. When $OD_{620}$ was 0.8, the seed broth was inoculated into a fermenter containing fermentation medium 2 (glucose 4%, potassium nitrate 0.1%, potassium dihydrogen phosphate 0.1%, ammonium sulfate 0.1%, and magnesium sulfate 0.1%), and the initial volume was 6 L after inoculation and the inoculum amount was 22%. 4% (v/v, relative to the initial volume of the fermentation) dodecane was added at the start of the fermentation. A temperature of 28° C., an aeration rate of about 0.6 vvm, and a tank pressure (gauge pressure) of about 0.10 MPa were controlled, and dissolved oxygen was controlled to be not below 20% in the fermentation process. The pH value of the fermentation broth was controlled by feeding liquid alkali at a concentration of 33%. Cells mainly grew at prophase of fermentation, and the pH was about 6.7 at the start of the fermentation; the pH of the fermentation broth gradually decreased with the growth of the microorganism, and the pH was controlled to be not below 3.0; and the pH was controlled to be about 6.0 when the optical cell density ($OD_{620}$) was above 0.5 (diluted 30 times), and a sugar solution at a concentration of 25% was fed and the sugar concentration in the fermentation broth was controlled to be 0.5%. The alkane was fed in batch when the fermentation period was 10 to 20 hours, and the alkane content in the fermentation broth was controlled to be not above 10%. The total fermentation period was about 122 hours, the acid production was 182.3 mg/g, the conversion rate by weight of a dicarboxylic acid to an alkane was 100.4%, and the alkali addition was 2.5 tons.

According to the determination methods as mentioned above, the salt content in the fermentation broth was 6.59%, and the salt content in the treated fermentation broth was 6800 ppm.

Example 9: Fermentation of DC13 with *Candida tropicalis* CAT H1614 in a 200 M³ Fermenter A tube of strain in glycerol was inoculated into a seed flask containing seed medium, and the pH was natural. The culture was cultivated in a shaker at 28° C. and 230 rpm for 2 days. A seed in shake flask was inoculated into a seed tank containing seed medium, and the inoculum amount was 10%. The initial pH value of the system after inoculation was 6.5. The culture was cultivated for 25 h at 28° C., with an aeration rate of 0.6 vvm and a tank pressure of 0.11 MPa. The pH naturally decreased to 3 during the culture. When $OD_{620}$ was 0.8, the seed broth was inoculated into a fermenter containing fermentation medium 2 (glucose 3.8%, potassium nitrate 0.12%, potassium dihydrogen phosphate 0.12%, ammonium sulfate 0.12%, and magnesium sulfate 0.12%), and the inoculum amount was 25%. 4% (v/v, relative to the initial volume of the fermentation) tridecane was added at the start of the fermentation. A temperature of 28° C., an aeration rate of about 0.6 vvm, and a tank pressure (gauge pressure) of about 0.10 MPa were controlled, and dissolved oxygen was controlled to be not below 20% in the fermentation process. The pH value of the fermentation broth was controlled by feeding liquid alkali at a concentration of 30%. Cells mainly grew at prophase of fermentation, and the pH was about 6.6 at the start of the fermentation; the pH of the fermentation broth gradually decreased with the growth of the microorganism, and the pH was controlled to be not below 3.0; and the pH was controlled to be about 6.5 when the optical cell density ($OD_{620}$) was above 0.5 (diluted 30 times) until the end of the fermentation. The alkane was fed in batch when the fermentation period was 10 to 20 hours, and the alkane content in the fermentation broth was controlled to be not above 10%. The total fermentation period was about 132 hours, the acid production was 147.3 mg/g, the conversion rate by weight of a dicarboxylic acid to an alkane was 85.4%, and the alkali addition was 3.7 tons.

According to the determination methods as mentioned above, the salt content in the fermentation broth was 8.1%, and the salt content in the treated fermentation broth was 6500 ppm.

Example 10: Fermentation of DC12 with *Candida tropicalis* CAT H1614 in a 450 M³ Fermenter A tube of the strain in glycerol was inoculated into a seed flask containing seed medium, and the pH was natural. The culture was cultivated in a shaker at 28° C. and 230 rpm for 2 days. A seed in shake flask was inoculated into a seed tank containing seed medium, and the inoculum amount was 10%. The initial pH value of the system after inoculation was 6.2. The culture was cultivated for 25 h at 28° C., with an aeration rate of 0.6 vvm and a tank pressure of 0.11 MPa. The pH naturally decreased to 3 during the culturing. When $OD_{620}$ was 0.8, the seed broth was inoculated into a fermenter containing fermentation medium 2 (glucose 3.3%, potassium nitrate 0.15%, potassium dihydrogen phosphate 0.15%, ammonium sulfate 0.15%, and magnesium sulfate 0.15%), and the inoculum amount was 23%. 5% (v/v, relative to the initial volume of the fermentation) dodecane was added at the start of the fermentation. A temperature of 28° C., an aeration rate of about 0.5 vvm, and a tank pressure (gauge pressure) of about 0.10 MPa were controlled, and dissolved oxygen was controlled to be not below 20% in the fermentation process. The pH value of the fermentation broth was controlled by feeding liquid alkali at a concentration of 33%. Cells mainly grew at prophase of fermentation, and the pH was about 6.5 at the start of the fermentation; the pH of the fermentation broth gradually decreased with the growth of the microorganism, and the pH was controlled to be not below 3.0; and the pH was controlled to be about 6.2 when the optical cell density ($OD_{620}$) was above 0.5 (diluted 30 times) until the end of the fermentation. The alkane was fed in batch when the fermentation period was 10 to 20 hours, and the alkane content in the fermentation broth was controlled to be not above 10%. The total fermentation period was about 142 hours, the acid production was 160.8 mg/g, the conversion rate by weight of a dicarboxylic acid to an alkane was 90.8%, and the alkali addition was 5 tons.

According to the determination methods as mentioned above, the salt content in the fermentation broth was 7.1%, and the salt content in the treated fermentation broth was 6500 ppm.

Example 11: Fermentation of DC12 with *Candida sake* CATH430 in a 450 M³ Fermenter A tube of the strain in glycerol was inoculated into a seed flask containing seed medium, and the pH was natural. The culture was cultivated in a shaker at 28° C. and 230 rpm for 2 days. A seed in shake flask was inoculated into a seed tank containing seed medium, and the inoculum amount was 10%. The initial pH value of the system after inoculation was 6.2. The culture was cultivated for 25 h at 28° C., with an aeration rate of 0.6 vvm and a tank pressure of 0.11 MPa. The pH naturally decreased to 3 during the culturing. When $OD_{620}$ was 0.8, the seed broth was inoculated into a fermenter containing fermentation medium 2 (glucose 3.3%, potassium nitrate 0.15%, potassium dihydrogen phosphate 0.15%, ammonium sulfate 0.15%, and magnesium sulfate 0.15%), and the inoculum amount was 23%. 5% (v/v, relative to the initial volume of the fermentation) dodecane was added at the start of the fermentation. A temperature of 28° C., an aeration rate of about 0.5 vvm, and a tank pressure (gauge pressure) of about 0.10 MPa were controlled, and dissolved oxygen was controlled to be not below 20% in the fermentation process. The pH value of the fermentation broth was controlled by feeding liquid alkali at a concentration of 33%. Cells mainly grew at prophase of fermentation, and the pH was about 6.5 at the start of the fermentation; the pH of the fermentation broth gradually decreased with the growth of the microorganism, and the pH was controlled to be not below 3.0; and the pH was controlled to be about 6.2 when the optical cell density ($OD_{620}$) was above 0.5 (diluted 30 times) until the end of the fermentation. The alkane was fed in batch when the fermentation period was 10 to 20 hours, and the alkane content in the fermentation broth was controlled to be not above 10%. The total fermentation period was 132 hours, the acid production was 152 mg/g, the conversion rate by weight of a dicarboxylic acid to an alkane was 90.2%, and the alkali addition was 5 tons.

According to the determination methods as mentioned above, the salt content in the fermentation broth was 8%, and the salt content in the treated fermentation broth was 6000 ppm.

Example 12

A method of preparing a long chain dicarboxylic acid comprises the following steps:

subjecting the fermentation broth produced in Example 9 to acidification by adjusting its pH to pH 3 with sulfuric acid so as to obtain a solid and a treated fermentation broth; centrifuging and separating the solid, wherein most of the solid are particles of a long chain dicarboxylic acid; then dissolving the solid in acetic acid, and adding activated carbon that is no more than 5% of the volume of the supernatant to decolorize for 60 min at 90° C.; filtering and obtaining the supernatant, and cooling the temperature of the supernatant down to 80° C. and keeping for 1.5 hours, and then cooling down to 35° C., and crystallizing; and obtaining the product of the dicarboxylic acid by centrifugation.

Example 13

A method of preparing a long chain dicarboxylic acid comprises the following steps:

subjecting the fermentation broth produced in Example 10 to acidification by adjusting its pH to pH 3.5 with sulfuric acid so as to obtain a solid and a treated fermentation broth; centrifuging and separating the solid, wherein the solid comprises particles of a long chain dicarboxylic acid and cells; then dissolving the solid in ethanol, and adding activated carbon that is no more than 5% of the volume of the supernatant to decolorize for 75 min at 95° C.; filtering and obtaining the supernatant, and cooling the temperature of the supernatant down to 80° C. and keeping for 1 hour, and then cooling down to 35° C., and crystallizing; and obtaining the product of the dicarboxylic acid by centrifugation.

Example 14

A method of preparing a long chain dicarboxylic acid comprises the following steps:

subjecting the fermentation broth produced in Example 11 to acidification by adjusting its pH to pH 3.2 with sulfuric acid so as to obtain a solid and a treated fermentation broth; filtering and obtaining the solid, wherein the solid comprises particles of a long chain dicarboxylic acid and cells; then dissolving the solid in ethanol, and adding activated carbon that is no more than 5% of the volume of the supernatant to decolorize for 70 min at 85° C.; filtering and obtaining the supernatant, and cooling the temperature of the supernatant down to 65° C. and keeping for 1 hour, and then cooling down to 35° C., and crystallizing; and obtaining the product of the dicarboxylic acid by centrifugation.

Based on the aforementioned examples, it can be seen that the fermentation of a long chain dicarboxylic acid by *Candida* strains provided by the present invention has the following advantages compared with the existing fermentation process: shorter fermentation time, less alkali consumption, and high dicarboxylic acid production; and that a large amount of dicarboxylic acid can be obtained directly by fermentation, which does not require the cumbersome extraction steps, and reduces the production process and material consumption, and the production cost of a long chain dicarboxylic acid can be reduced greatly and it is environmental friendly.

It is obvious to those skilled in the art that various modifications and changes can be made to the present invention without departing from the scope and spirit of the present invention, and combinations of the above various technical features and other changes of technical solutions achieved according to the above contents are within the scope of the present invention.

What is claimed is:

1. A method for producing a long chain dicarboxylic acid by fermentation, characterized in that the content of salt in the fermentation broth is controlled to be below 20%, wherein the percentage is a mass percentage relative to the total amount of the long chain dicarboxylic acid produced by fermentation, wherein the pH of the fermentation system is controlled to be below 6.2 until the end of the fermentation, when the optical cell density $OD_{620}$ of the cells diluted 30 times is above 0.5 in the fermentation process, wherein the substrate comprises a C9 to C22 normal alkane, and the long chain dicarboxylic acid comprises a C9 to C22 long chain dicarboxylic acid.

2. The method of claim 1, characterized in that the salt comprises one or more of potassium salt, sodium salt, magnesium salt, calcium salt, iron salt, ammonium salt, hydrochloride, carbonate, sulfate, nitrate and phosphate.

3. The method of claim 1, characterized in that the pH during trophophase of the fermentation is above 3.0; and/or the pH during conversion phase of the fermentation is between 4.0 and 6.2.

4. The method of claim 1, characterized in that the temperature of the fermentation is between 28 and 32° C.; and/or the aeration rate of the fermentation is between 0.3 and 0.7 vvm; and/or the pressure of the fermentation is between 0.05 and 0.14 MPa; and/or the dissolved oxygen in the conversion process of the fermentation is not less than 15%; and the inoculum amount of the fermentation is between 10% and 30%.

5. The method of claim 1, characterized in that the strain for fermentation comprises *Candida tropicalis* or *Candida sake*.

6. A method for preparing a C9 to C22 long chain dicarboxylic acid, comprising the following steps:
   (1) obtaining a fermentation broth of a long chain dicarboxylic acid according to the method for producing a long chain dicarboxylic acid by fermentation of claim 1;
   (2) acidifying the fermentation broth obtained in step (1) to obtain a solid and a treated fermentation broth, and separating and then dissolving the solid in an organic solvent, and separating a supernatant and crystallizing to obtain a product of the long chain dicarboxylic acid.

7. The method of claim 6, characterized in that the pH of the acidification is between 2.5 and 5;
   and/or, the method for separating is centrifugation or filtration;
   and/or, the organic solvent comprises one or more of an alcohol, an acid, a ketone and an ester; wherein the alcohol comprises one or more of methanol, ethanol, isopropanol and n-butanol; the acid comprises acetic acid; the ketone comprises acetone; and the ester comprises ethyl acetate and/or butyl acetate;
   and/or, after dissolving in an organic solvent, decolorizing and then separating the supernatant;
   and/or, the crystallization is cooling crystallization, comprising the following steps: cooling down to between 65 and 80° C., and keeping for 1 to 2 hours, then cooling down to between 25 and 35° C., and crystallizing;
   and/or, a product of the dicarboxylic acid is obtained by separation after crystallization;
   and the method of separation is centrifugation.

8. A product, which is one of the following products I) to III):
   I) a fermentation broth of a C9 to C22 long chain dicarboxylic acid, characterized in that the content of salt in the fermentation broth of a long chain dicarboxylic acid is below 20%, wherein the percentage is a mass percentage relative to the total amount of the long chain dicarboxylic acid produced by fermentation;
   II) a treated fermentation broth of a C9 to C22 long chain dicarboxylic acid, characterized in that the content of salt in the treated fermentation broth is below 12000 ppm, wherein the parts per million (ppm) is the parts per million by mass of the salt to the treated fermentation broth of the long chain dicarboxylic acid, wherein the treated fermentation broth is obtained by removing a solid in the fermentation broth of a long chain dicarboxylic acid in I), wherein the solid comprises a particle of the long chain dicarboxylic acid;
   III) a wastewater produced by a method for producing a C9 to C22 long chain dicarboxylic acid by fermentation, characterized in that the content of salt in the wastewater is below 12000 ppm, wherein the parts per million is the parts per million by mass of the salt to the wastewater, wherein the wastewater is a liquid that enters into a wastewater treatment system, obtained by removing a solid in the fermentation broth of a long chain dicarboxylic acid in I).

9. The product of claim 8, which is I) the fermentation broth of a long chain dicarboxylic acid, wherein the fermentation broth of a long chain dicarboxylic acid is a fermentation broth of a long chain dicarboxylic acid obtained by fermentation conversion under an acidic condition.

10. The method of claim 1, wherein the pH during the conversion phase of the fermentation is between 5.0 and 6.2.

11. The method of claim 1, characterized in that the pH of the fermentation system is controlled to be between 4.0 and 6.2.

12. The method of claim 1, wherein the long chain dicarboxylic acid comprises a C9 to C18 long chain dicarboxylic acid.

13. The method of claim 6, further comprising controlling the content of salt in the treated fermentation broth to be below 12000 ppm by acidification, wherein the parts per million (ppm) is the parts per million by mass of the salt to the treated fermentation broth of the long chain dicarboxylic acid.

14. The method of claim 6, wherein the solid comprises a particle of the long chain dicarboxylic acid, or the solid comprises a particle of the long chain dicarboxylic acid and a cell.

15. The method of claim 7, wherein the method for decolorizing is an activated carbon decolorization, wherein the amount of the added activated carbon is no more than 5% of the volume of the supernatant, the temperature of the decolorization is between 85 and 100° C.; and the decolorization time is between 15 and 165 min.

16. The product of claim 8, which is I) the fermentation broth of a long chain dicarboxylic acid, wherein the content of salt in the fermentation broth of a long chain dicarboxylic acid is below 15%.

17. The product of claim 9, wherein the fermentation broth of a long chain dicarboxylic acid is a fermentation broth of a long chain dicarboxylic acid obtained by fermentation conversion at a pH below 6.2.

18. The product of claim 9, wherein the fermentation broth of a long chain dicarboxylic acid is a fermentation broth of a long chain dicarboxylic acid obtained by fermentation conversion at a pH between 4.0 and 6.2.

19. The product of claim 9, wherein the fermentation broth of a long chain dicarboxylic acid is a fermentation broth of a long chain dicarboxylic acid obtained by fermentation conversion at a pH between 5.0 and 6.2.

20. The method of claim 1, wherein the pH of the fermentation system is controlled to be below 4.0 until the end of the fermentation.

* * * * *